United States Patent [19]
Strohmaier

[11] Patent Number: 5,356,290
[45] Date of Patent: Oct. 18, 1994

[54] MEDICAL TREATMENT DEVICE, IN PARTICULAR FOR SURGICAL PURPOSES

[75] Inventor: Ernst Strohmaier, Bad Schussenried, Fed. Rep. of Germany

[73] Assignee: Kaltenbach & Voigt GmbH & Co., Biberach/Riss, Fed. Rep. of Germany

[21] Appl. No.: 981,364

[22] Filed: Nov. 25, 1992

[30] Foreign Application Priority Data

Nov. 25, 1991 [DE] Fed. Rep. of Germany ....... 4138681

[51] Int. Cl.$^5$ .............................................. A61G 15/00
[52] U.S. Cl. ..................................................... 433/77
[58] Field of Search ...................... 433/77, 98, 99, 126, 433/131

[56] References Cited

U.S. PATENT DOCUMENTS

| | | | |
|---|---|---|---|
| 3,978,586 | 9/1976 | Etherington | 433/131 |
| 4,354,839 | 10/1982 | Schuss | 433/126 |
| 4,515,564 | 5/1985 | Lohn | 433/126 |
| 4,518,355 | 5/1985 | Hoffmeister et al. | 433/126 |
| 4,669,982 | 6/1987 | Fleer | 433/126 |

FOREIGN PATENT DOCUMENTS

3215255 10/1983 Fed. Rep. of Germany .

*Primary Examiner*—Cary E. O'Connor
*Attorney, Agent, or Firm*—Scully, Scott, Murphy & Presser

[57] ABSTRACT

In a medical treatment device for a treatment station, consisting of a motor-operated treatment instrument having a hand piece consisting of at least two portions, of which the one hand piece portion can be connected to a control unit by means of a media supply line and the other hand piece portion is used to receive a treatment tool, one of the two hand piece portions contains a separable motor cartridge and associated with the treatment location there is a receiving arrangement for the motor cartridge, to which arrangement the motor cartridge can be transferred using the hand piece portion which supports the cartridge and from which the motor cartridge can be transferred back again using the hand piece portion which supports the cartridge.

13 Claims, 5 Drawing Sheets

MEDICAL TREATMENT DEVICE, IN PARTICULAR FOR SURGICAL PURPOSES

TECHNICAL FIELD OF THE INVENTION

The invention relates to a medical treatment device, in particular for surgical purposes.

BACKGROUND OF THE INVENTION AND PRIOR ART

When treating a human or animal body, it can be presumed that the treatment instrument will be contaminated with disease-causing agents originating from the body. This applies both to such treatment instruments with which the body can be treated at a distance, for example spray nozzles, and in particular to such treatment instruments during the use of which direct contact occurs with the body. In particular contamination of the treatment instrument can be reckoned with when the treatment instrument comes into contact with body fluids, for example blood, as is the case in particular in the case of treatment with a surgical treatment instrument.

It is therefore the intention to sterilize the treatment instrument including its supply hose, through which the necessary driving energy and, if applicable, a treatment agent, in particular a coolant or the like, are fed.

The hand piece of a treatment instrument can consist of a drive portion with a fixedly installed motor and a tool carrier portion, it being possible to couple the drive portion and the tool carrier portion together in a releasable manner. Various tool carrier portions, predestined for respective treatments, can thus be selectively connected with the drive and be detached again.

For the purposes of sterilization, steam sterilization at up to 3 bar pressure at a temperature of 145° C., for example, is usual.

A complicated construction of the motor and of the receiving portion which receives it at the drive portion is required for a sterilization-proof construction of the motor, as otherwise sterilizing agent is able to penetrate into the motor which impairs the bearing and functional parts which are present and thus substantially reduces the life of the treatment instrument. A construction of the motor which is absolutely secure against entry of sterilizing agent is difficult and expensive, so high costs of production have to be reckoned with.

OBJECT OF THE INVENTION

The object of the invention is to develop a treatment device of the kind specified at the beginning such that the motor can be set free from the treatment instrument, with ease of handling, for the sterilization of said treatment instrument.

SUMMARY OF THE INVENTION

According to the present invention there is provided a medical treatment device for a treatment station, in particular for surgical purposes, consisting of a motor-operated treatment instrument having a hand piece consisting of at least two portions, of which the one hand piece portion can be connected to a control unit by means of a media supply line and the other hand piece portion is used to receive a treatment tool, wherein one of the two hand piece portions contains a separable motor cartridge and associated with the treatment station there is a receiving arrangement for the motor cartridge, to which arrangement the motor cartridge can be transferred using the hand piece portion which supports the cartridge and from which the motor cartridge can be transferred back again using the hand piece portion which supports the cartridge.

In the case of the treatment instrument according to the invention, a motor cartridge is releasably coupled to the drive portion, and provided in the region of the treatment station there is a parking position with a receiving arrangement for the motor cartridge onto which or into which the motor cartridge can be delivered and removed again, with ease of handling. For this, the motor cartridge does not need to be gripped directly by hand.

With the presence of a releasable coupling between the sleeve of the hand piece and the motor cartridge and/or between the latter and the receiving arrangement, it is possible in a particularly safe manner to deliver the motor cartridge to the receiving arrangement using the handpiece, and to take it up again from said arrangement.

As the motor cartridge is received in the sleeve of the hand piece, preferably so as to be enclosed or fully covered, contamination of the motor cartridge is prevented. As, moreover, the motor cartridge can be deposited at the parking location without any further manual contact and remote from the body to be treated, sterile handling of the motor cartridge is ensured, in which case the hand piece and the supply hose can be sterilized. Subsequently, the motor cartridge is taken up with the pertinent portion of the sterilized hand piece and the hand piece is completed ready for use.

Within the scope of the invention it is possible to provide the sleeve of the hand piece at the drive portion or at the tool carrier portion. In both cases, it is possible to deposit the motor cartridge at the parking location without directly gripping it manually, using the corresponding hand piece portion, and to take it up again.

It is known per se from European patent No. 0 183 972 to provide a motor cartridge for a dental hand piece, but in the case of this known construction it is a question of being able to connect one and the same drive portion of a hand piece to several work piece carrier portions of different manufacturers and therefore of different forms and connection configurations whilst ensuring a media transfer. In the case of the one tool carrier portion a coupling sleeve is provided at the rear, into which sleeve the motor cartridge can be inserted. In the case of another tool carrier portion a separate coupling sleeve can be coupled to the tool carrier portion at the rear and the motor cartridge can be inserted into said sleeve at the rear, it being possible to connect the coupling sleeve at the rear to the front end of the drive portion.

Embodiments of the invention contain features which further improve the solution to the problem according to the invention, comprise simple and cost-favourable individual developments and improve the ease of handling and also functional reliability.

The invention also provides a treatment instrument in the form of a hand piece, in particular for an existing treatment device, consisting of two instrument portions which can be coupled together in a releasable manner and between which a drive in the form of a motor cartridge can be coupled in a releasable manner, in order to separate and, for example, not to sterilize it.

BRIEF DESCRIPTION OF THE DRAWINGS

The invention and further advantages which can be attained by it are explained in greater detail in the following with the aid of preferred exemplary embodiments and the drawings.

DETAILED DESCRIPTION OF PREFERRED EMBODIMENTS ACCORDING TO THE INVENTION

Figure 1:
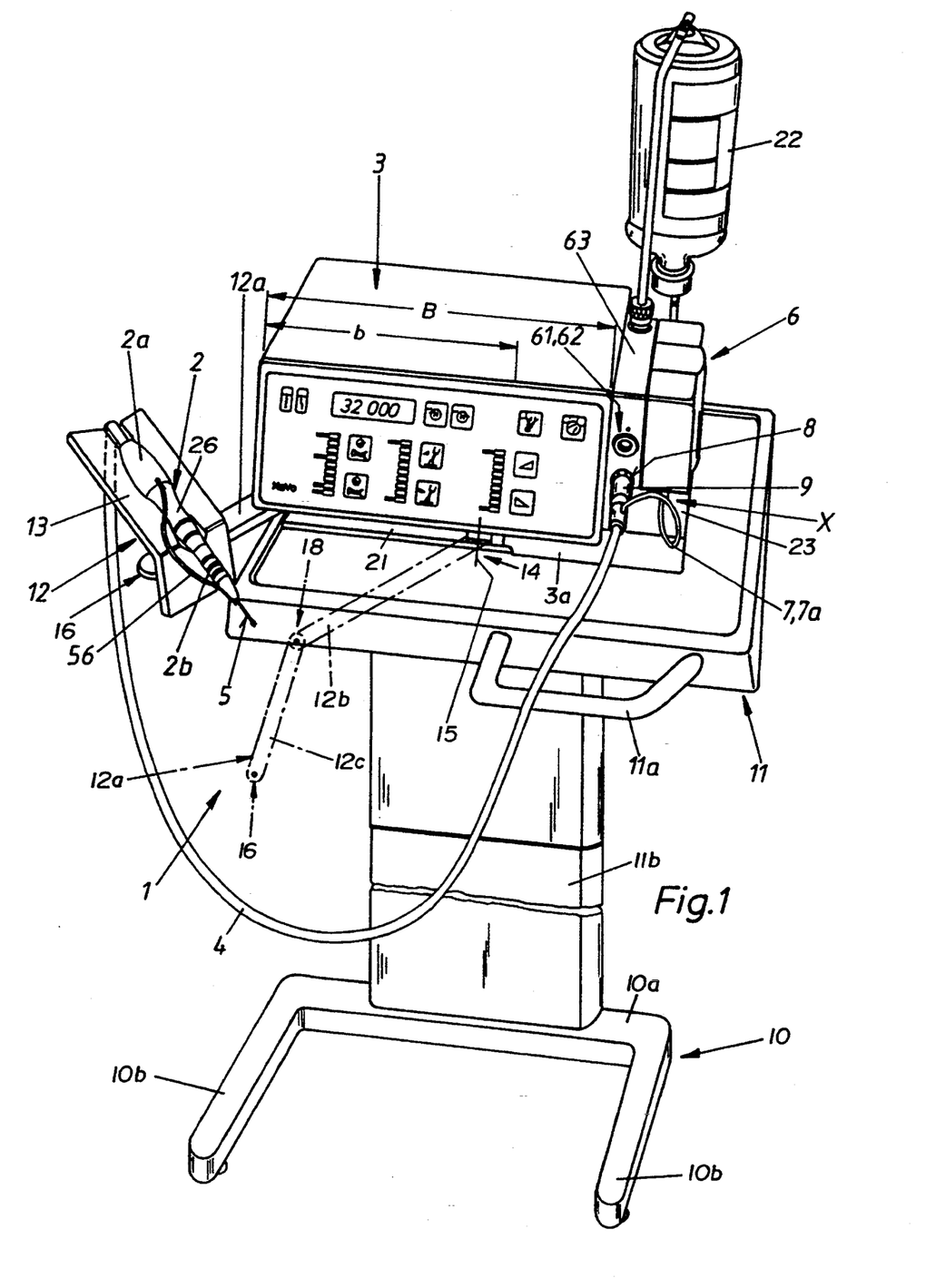
FIG. 1 shows, in a perspective representation, a medical treatment device according to the invention with a treatment instrument and a control device, connected therewith by means of a supply line, for a medical treatment station.

The main portions of the treatment device 1 are a treatment instrument in the form of a hand piece 2 and a control unit 3 with control keys on its front side and with an integrated electronic control device to which the hand piece 2 is connected by means of a bendable or flexible supply line 4. The hand piece 2 bears at its front end a treatment tool 5 which can preferably be exchanged for different, selectively required tools. In the case of such treatment instruments in which the feed of a coolant, in particular a cooling fluid such as a salt solution (NaCl), to the treatment position is required, associated with the control unit 3 there is a coolant pump 6 which can preferably be added on to the control unit 3 or can be integrated in said unit. The coolant line 7, which leads to the front end of the hand piece 2, extends at least in part through the supply line 4 and the hand piece 2 respectively. Arranged on the control unit 3 there is a plug-in coupling 8 into which a plug 9, which is arranged at the free end of the supply line 4, can be plugged for the purposes of connection to the electronic control device. The control unit 3 can stand on a frame or table 11. A holding arrangement 12 with a depository portion for the hand piece 2 in the latter's stand-by position is preferably arranged at the control unit 3. In the case of the present development, a depository portion is provided in the form of a trough-shaped, oblique shell or plate 13 which is inclined towards the treatment location and on which the hand piece 2 is supported in a form-fitting manner in a position with the tool 5 pointing obliquely downwards. The hand piece 2 is secured against lateral displacement on account of the trough-shaped form of the plate 13. The trough base is preferably adapted to the waisted form of the hand piece 2 so that a form-fitting support also results in the longitudinal direction of the latter. The plate 13 is held on a supporting arm 12a, which projects away from the table 11 or from the housing of the control unit 3 in an approximately horizontal manner, and is freely pivoted at the end of said arm preferably in a joint about an approximately vertical swivel axis.

The table 11 stands on the ground with rollers (not illustrated) and can be displaced by gripping it manually preferably at a front-side handle 11a. The table 11 is supported on the upper end of a supporting column 11b which stands on the cross-piece portion 10a of a U-shaped standing frame 10, the leg portions 10b of which point towards the operating side.

The supporting arm 12a is variable in terms of its length and is connected with the control unit 3 at its end which is remote from the holding arrangement 12 in an articulated joint 12d which is pivotable about a vertical swivel axis 12e. On account of this development, the holding arrangement 12 with the hand piece 2 can not only be swung freely horizontally, but can also be set in respect of its distance from the control unit 3. As a result, it is freely adjustable within a large range of movement and can be set in selective stand-by positions which are favourable relative to the treatment location or the treatment position and in which the person effecting the treatment can grip the hand piece with ease of handling and deposit it again. In the drawing, the supporting arm 12 is represented with broken lines in its drawn-out position. In the case of this outline representation, the holding arrangement 12 is omitted in order to show the joint supporting it at the free end of the supporting arm 12a, that can be formed by means of a vertical bore in which a round peg (not illustrated) projecting downwards from the holding arrangement 12 can be plugged from above with play for movement.

Within the scope of the invention, the supporting arm 12a can be a supporting arm which can be telescoped. In the case of the present development, the supporting arm 12a is formed in the sense of an articulated lever with two supporting arm portions 12b, 12c which are connected with each other at their facing ends in a central joint about a vertical swivel axis. The two connected ends of the supporting arm portions 12b, 12c preferably lie one on top of the other, in which case they overlap and a joint pin is set through them in vertical bores. It is advantageous, on the one hand, on account of savings in space and, on the other hand, for reasons of attaining sufficient stability, to form the supporting arm portions 12b, 12c out of planar strips of rectangular cross section which are arranged in a planar manner.

It is advantageous to mount the supporting arm 12a in such a way that in its pushed-in or swung-in position it renders possible an arrangement of the plate 13 as close as possible to the control unit 3. It is possible in this regard to arrange or mount the supporting arm 12a above the control unit 3 in order to be able to swing it in above the control unit 3 in the vertical range of projection of the latter, if applicable with the holding arrangement 12, whereby a configuration saving much space is created. It is also possible to arrange or mount the supporting arm 12a in a free space (not illustrated) which exists below the control unit, in which case such a free space could be created by spacers between the control unit 3 and the table 11. In the case of the present development, a horizontal recess 20 is provided in the lower region of the box-shaped control unit, here below the control or keyboard panel, into which recess the supporting arm 12a can be swung. In this connection, the joint 14 can be arranged in the region of the front side of the control unit 3 or within the recess 20, as illustrated in the drawing. In the case of the present development the recess 20 is arranged in the front left corner region of the control unit 3 and it is accessible or open both on the operating side, that is, from the front and from the left side. The width b of the recess 20 which extends from the left side of the control unit 3 towards the right corresponds to substantially three quarters of the width B of the control unit 3 so that the recess 20 ends at a distance from the right side of the control unit 3. In the swung-in position the plate 13 is located directly in front of the right half of the front side of the control unit 3. The height of the recess 21 is dimensioned to be so large that the supporting arm 12a can be swung in with vertical play for movement.

The width b of the recess 20 and the length of the inner supporting arm portion 12b are preferably matched to each other in such a way that in the swung-in position according to FIG. 1 the inner supporting arm portion 12b or the central joint 18 do not project laterally out of the recess 21.

The recess 20 is preferably formed in a support which in particular is plate-shaped, here in a base plate 3a of the box-shaped control unit 3. The base plate 3a can be secured to the control unit 3 in a detachable manner, for example by means of screws. The arrangement or the control unit 3 respectively can thus be completed in a modular fashion by means of the base plate 3a which can be added, if applicable with the holding arrangement 12, or be selectively retrofitted.

The previously described configuration and development of the holding arrangement 12 renders possible selective setting of the stand-by position of the hand piece 2 in the whole front region of the control unit 3. The stand-by position of the holding arrangement 12 to be selected can thus be adapted to a plurality of, and even difficult, treatment positions.

Figure 5:
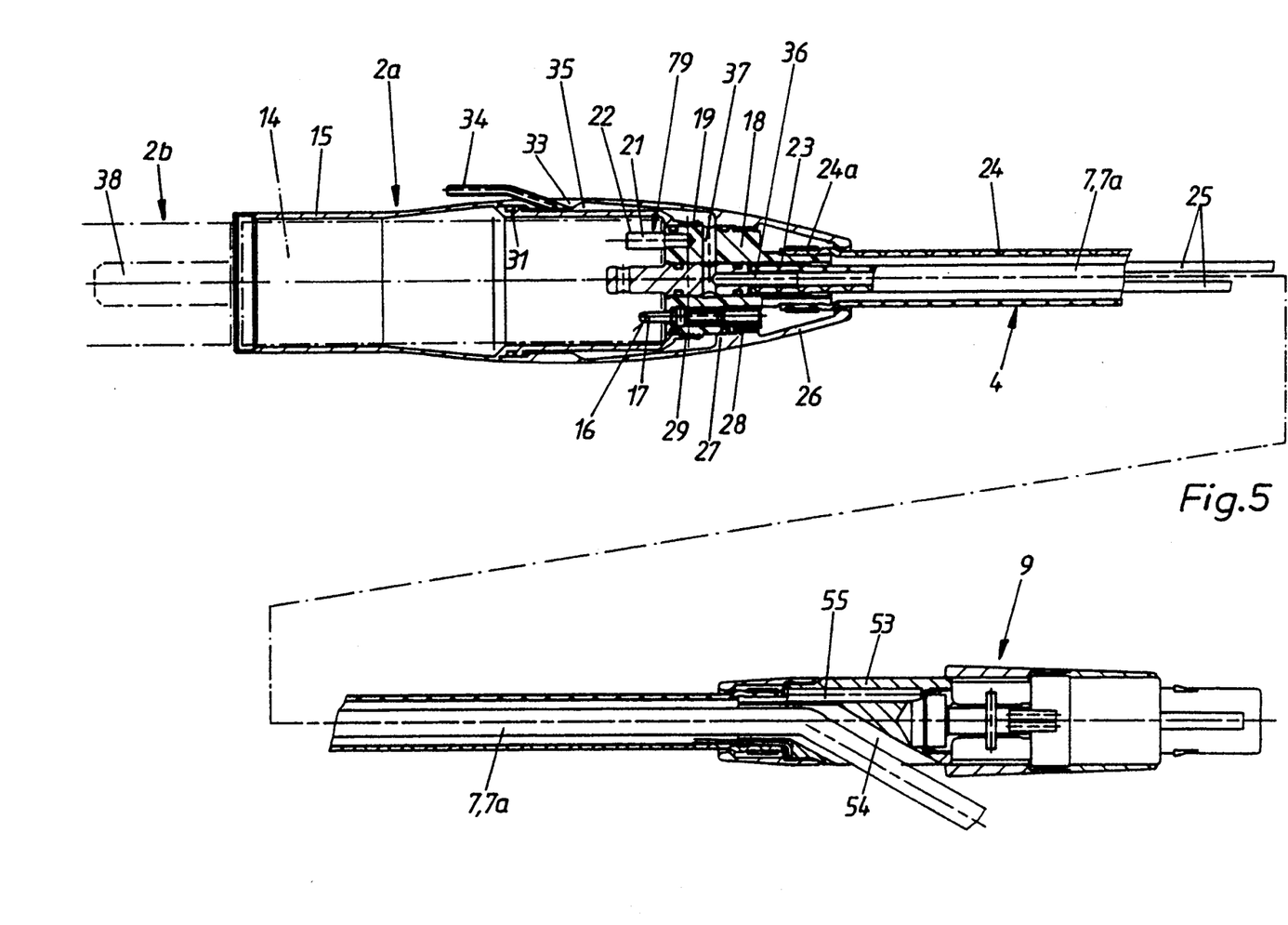
FIG. 5 shows the drive portion of the two-piece treatment instrument with associated supply line, in a longitudinal section.

The hand piece 2 consists of two portions which are arranged one after the other in its longitudinal direction, namely a drive portion 2a, which is mounted on the supply line 4, and a work piece carrier portion 2b which can be releasably secured to the drive portion's front end by means of a rapid-action coupling. Arranged in the drive portion 2a there is a suitable drive motor, for example an electric motor or a compressed-air operated turbine motor, which is encapsulated in a housing in the form of a motor cartridge 14, in the manner of a cartouche. The drive portion 2a, for the purpose of accommodating the engine cartridge 14, has a cylindrical sleeve 15 which is open on the front side and the longitudinal dimensions of which are such that it completely covers at least the housing of the motor cartridge 14. Provided on the rear side of the motor cartridge 14 there are two contact elements, preferably lying diametrically opposite each other, in particular in the form of plug-in couplings 16 which correspond with two contact elements in the form of contact pins 17 which protrude from the base of the sleeve parallel to the axis. The contact pins 17 are plugged in a housing insert piece 18 which is round in cross section, sits in an annular collar 19 arranged at the rear end of the sleeve 15 and is secured by means of a screw which is set through the annular collar 19, projecting from the rear, radially in a hole. The insert piece 18 consists of electrically non-conductive material, in particular plastics material. There projects, moreover, from the insert piece 18 parallel to the axis a positioning pin 21 which fits into a corresponding positioning hole 22 at the rear end of the motor cartridge 14. The positioning pin 21 is arranged so as to be offset in the circumferential direction relative to the contact pins 17 and for the purposes of illustration is displaced into the sectional plane so that only one contact pin 17 is visible. The insert piece 18 has at the rear a tapered cylindrical extension 23 on which a flexible protective hose 24 is plugged and secured by means of a hose clip 24a or the like. There extend in the protective hose 24, according to the embodiment, several conductors, for example two electric cables 25, the cores of which are connected with the contact pins 17 in a manner which is not represented, a coolant hose 7a, and, if applicable, a light guide, all constructed in a flexible manner.

The drive portion 2a has two housing portions which are arranged coaxially relative to each other, namely, on the one hand, the sleeve 15 and a sleeve cap 26 which is at the rear relative to the sleeve and which engages over the rear end region or the rear half of the sleeve 15, covers the insert piece 18 and extends as far as the free end region of the extension 23 where it surrounds the protective hose 24 with play for movement. The sleeve cap 26 has substantially in its central region an inner ring extension 27 with a cylindrical inner face 28 which is preferably dimensioned so as to be somewhat smaller in diameter compared with the cylindrical inner face 29 of the ring extension 19. Provided in the rear region of the insert piece 18 between the latter and the ring extension 27 there is an inner thread/outer thread with which the sleeve cap 26 can be screwed on from the rear. The front end of the sleeve cap 26, which is round in cross section, sits on a cylindrical outer ring extension 31 and is sealed by means of a sealing ring (O-ring) which is arranged in a groove preferably in the outer ring extension 31. The inner faces of the ring extension 19 and inner ring extension 27 are also sealed each by means of a respective O-ring which sits in a groove in the insert piece 18. Located behind the front free edge region of the sleeve cap 26 there is a further inner ring extension 33 which is penetrated by a bore which extends obliquely towards the front and outside and in which the rear end of a small tube 34 is inserted in a firm and tight manner, which tube is angled outside the sleeve cap 26 approximately axis-parallel towards the front. Between the outer ring extension 31 and the inner ring extension 27 there extends between the sleeve 15 and the sleeve cap 26 a free annular space 35 from which the small tube 34 issues and which forms a section of the coolant line 7. The latter is connected with the annular space 35 by means of a channel section 36 which extends axially and a channel section 37 which extends radially in the insert piece 18.

Figure 6:
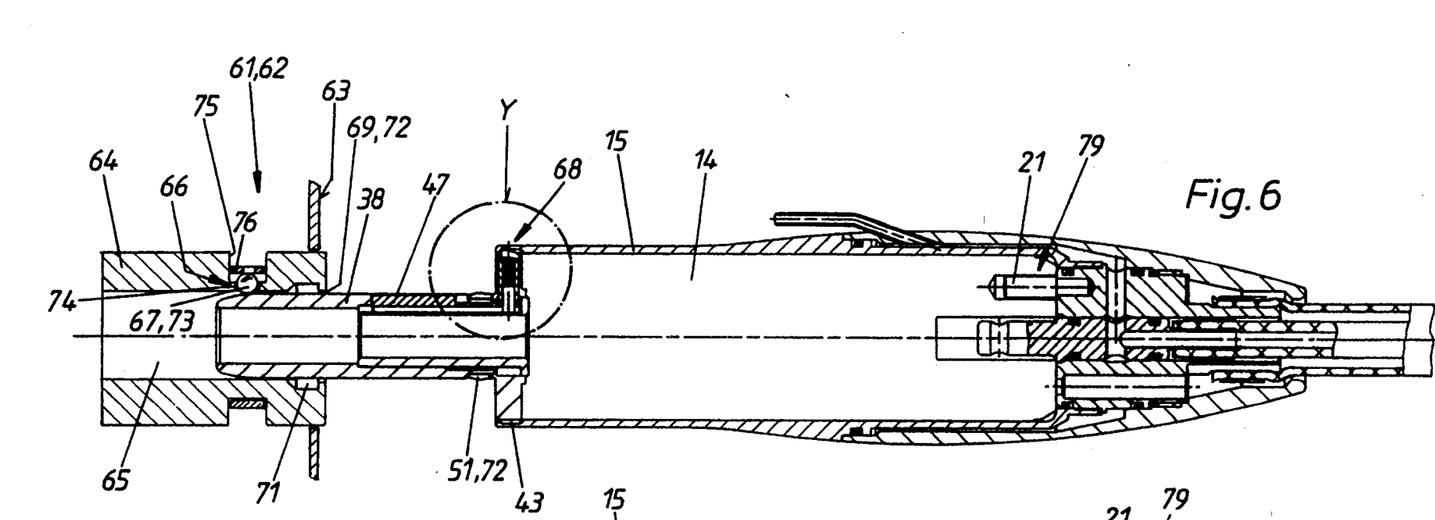
FIGS. 6 and 7 show a parking position with a receiving arrangement for a motor cartridge of the hand piece in two different functional dispositions.
Figure 8:
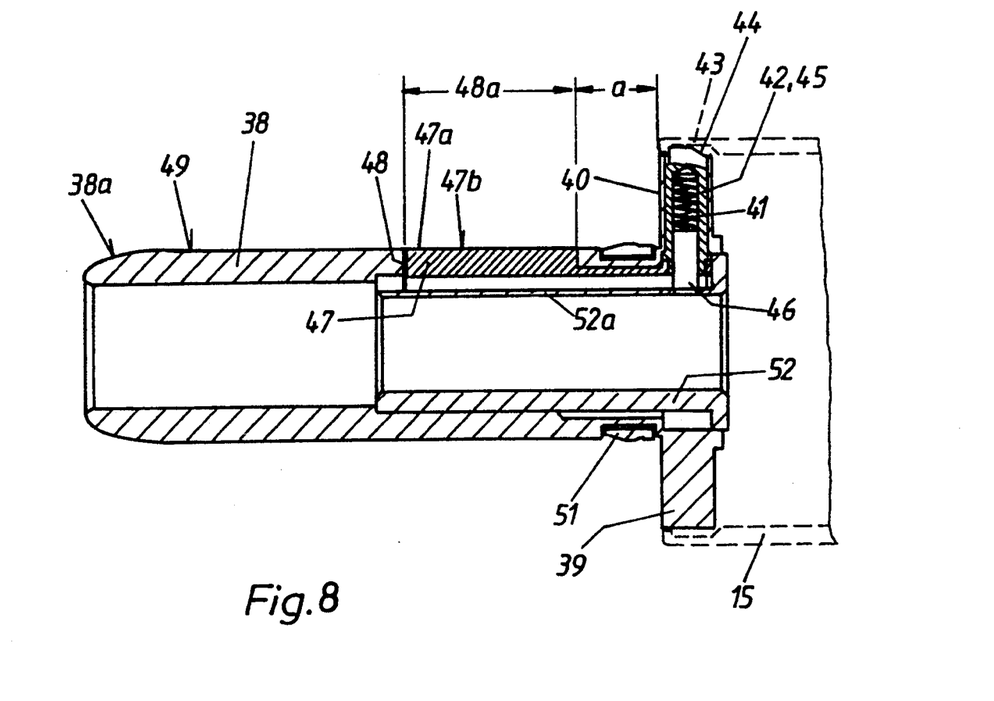
FIG. 8 shows the detail characterised in FIG. 6 by Y in an enlarged representation.

As FIGS. 5, 6 and 8 show best, the motor cartridge 14 has a coaxial front sleeve plug 38 which with a rear flange 39 is flange-mounted on the motor cartridge 14 preferably by means of screws which are parallel to the axis.

The motor cartridge 14 can be locked in the sleeve 15, preferably in the position in which it is entirely inserted, so as to be releasable axially. As can be inferred in particular from FIGS. 6 and 8, a locking pin 41 is used for this, which pin is mounted in the flange 39 so as to be radially displaceable in a bore hole 40 in the flange 39, has a spring 42 acting upon it radially towards the outside and is able to engage into an annular groove 43 which is arranged at the front end of the sleeve 15. For the purpose of facilitating the engagement, the locking pin 41 has a run-on slope 44 on the rear side. The spring 42 is preferably a pressure spring which is arranged in a blind bore hole 45, which is closed radially towards the outside by means of the locking head, in the locking pin 41 and is supported radially towards the interior on the sleeve plug 38 or on a pin 46 which projects into the blind bore hole 45. The locking pin 41 is connected, preferably in one piece, with a bar-shaped pressure piece 47 which projects towards the front from the lower end of the locking pin, is preferably of approximately rectangular cross section and is mounted so as to be radially displaceable in an axial guide groove in the sleeve plug 38 with the locking pin 41. The guide groove 48 is open radially towards the outside at a distance a from the flange 39 in the direction of the front, the pressure piece 47 engaging radially outwardly into this guide groove section 48a with a radial pressure piece extension 47a, and in the pushed-out position terminating at the lateral surface 49 with its outer surface 47b, which is adapted to the curvature of the lateral surface 49 of the sleeve plug 38. Within the space a, a tensioning ring 51 is mounted on the sleeve plug 38 in a peripheral groove, projecting slightly in its radially relaxed position beyond the lateral surface 49 with a tensioning bead. The guide groove 48 is formed partly in the sleeve plug 38 and partly in a sleeve bushing 52 which is inserted fixedly into the sleeve plug 38 from the rear, with the guide groove 48 being closed radially on the inside by means of a cross-piece 52a of the sleeve bushing 52. The front outer edge of the sleeve plug 38 at 38a is shaped in a conical fashion or is rounded.

The coolant hose 7a in the region of the plug 9, preferably in a rear tapered connection piece 53 of the same, is guided obliquely outwards, an oblique channel 54 in the connection piece 53 being used for this purpose, issuing from the present central connection piece channel 55.

A small hose 56 (FIG. 1, FIG. 4) is provided in order to route the coolant from the small tube 34 to the tool carrier portion 2b, which small hose at the rear is plugged onto the small tube 34 and at the front is connected with a hose connection, preferably likewise in the form of a small tube, preferably in the front region of the tool carrier portion 2b. The section of the coolant hose 7a, which is guided obliquely out of the plug 9, is connected with its rear end to a line connection of the pump 6.

In order to increase the grip-stability, the drive portion 2a is formed so as to be slightly bulged. Preferably its front third is formed so as to be cylindrical and its other section is formed so as to be bulged.

In particular in the case of surgical treatment of a body with the treatment tool 5, it is can be assumed that the hand piece 2 will be contaminated with disease-causing agents. That is why the procedure is adopted to sterilize not only the treatment tool 5 and the tool carrier portion 2b, but also the drive portion 2a and the supply line 4 after each treatment. This can take place, for example, in an autoclave at a steam pressure of approximately 3 bar and a temperature of approximately 145° C. or in a sterilization fluid. An electric drive motor or a motor cartridge 14 is suited for such sterilization treatment only if it has very complicated sealing means which in addition must be heat-resistant, the cost of said sealing means greatly increasing the price of the treatment device. It has therefore been proposed that the motor cartridge 14 be protected from contamination and be exempted from the sterilization treatment. A parking position 61 with a receiving arrangement 62 for the motor cartridge 14 is used for this purpose during the sterilization of at least the treatment tool 5 and the tool carrier portion 2b and preferably also the drive portion 2a with the supply line 4. The parking position 61 or the associated parking location with the receiving arrangement 61 are preferably arranged at the control unit 3 so that a further item of the existing treatment station does not need to be specifically developed. The parking position 61 with the receiving arrangement 62 is preferably arranged on the front side of the control unit 3. It is also advantageous to form the receiving arrangement 62 on the pump 6 or on a connection plate 63 supporting the latter, which plate is arranged between the control unit 3 and the pump 6, preferably on the side of the control unit 3, and in particular can have the plug-in coupling 8 for the plug 9 on its front side as well. In the case of the present development, the plug-in coupling 8 is arranged below the receiving arrangement 62 on the connection plate 63. The receiving arrangement 62 is preferably formed by means of a plug-in bushing 64 with a plug-hole 65 which is accessible from the outside and is arranged in the connection plate 63 (see FIGS. 6 and 7). The plug-hole 65 is dimensioned to be so large that the sleeve plug 38 of the motor cartridge 14 can be plugged therein with play for movement.

With the receiving arrangement 62 there is a coupling means 66 for the releasable coupling of the motor cartridge 14 to the receiving arrangement 62 and an uncoupling actuating means 67 for the release of the first coupling 68 effective between the motor cartridge 14 and the sleeve 15 and established by the locking pin 41 and the annular groove 43.

The coupling means 66 are formed by a locating edge 69 at the outer end of the plug-in bushing 64 or the plug-hole 65 respectively, behind which edge an annular groove 71 is arranged in the plug-in bushing 64, into which groove, if applicable, the tensioning ring 51 is able to engage with its annular bead in a resilient and thus releasable manner. As a result, a second coupling 72 is established which is automatically effective in the position of the motor cartridge 14 in which the cartridge is plugged into the receiving arrangement 62, and secures said cartridge at the receiving arrangement 62 in a releasable manner.

The uncoupling actuating means 67 are formed by means of a pressure member 73 which is integrated in the receiving arrangement or plug-in bushing 64 respectively at such a distance from the outer end that it is able to press radially inwards against the pressure piece 47. The pressure force of the pressure member 73 is greater than the coupling closing force of the first coupling 68, that is, greater than the force of the spring 42 acting upon the locking pin 41 and the pressure piece 47 in their coupling position.

The pressure member 73 is preferably a sphere which can be moved radially inwards in a hole 74, which is dimensioned to be somewhat smaller than the diameter of the sphere, in the plug-in bushing 64 to such an extent that it is able to enter the plug-hole 65 to an extent greater than the uncoupling movement of the pressure piece 47 or the annular pin 41 respectively. In the case of the present development, the hole 74 is located in the base of an outer peripheral groove 75 of the plug-in bushing 64 in which a pressure spring ring 76 is arranged with play for movement, extends over the pressure member 73 and acts elastically upon the latter radially inwards.

The previously described first coupling 68 between the drive portion 2a and the motor cartridge 14, the second coupling 72 between the motor cartridge 14 and the receiving arrangement 62 and the uncoupling actuating means 67 for releasing the first coupling 68 render possible deposition of the motor cartridge 14 at the parking position 61, with ease of handling, for the purpose of sterilizing the drive portion 2a with its supply line 4 and also return-delivery of the motor cartridge 14 to the drive portion 2a with ease of handling. With this delivery and return-delivery, the motor cartridge 14 does not need to be handled separately manually.

Figure 2:
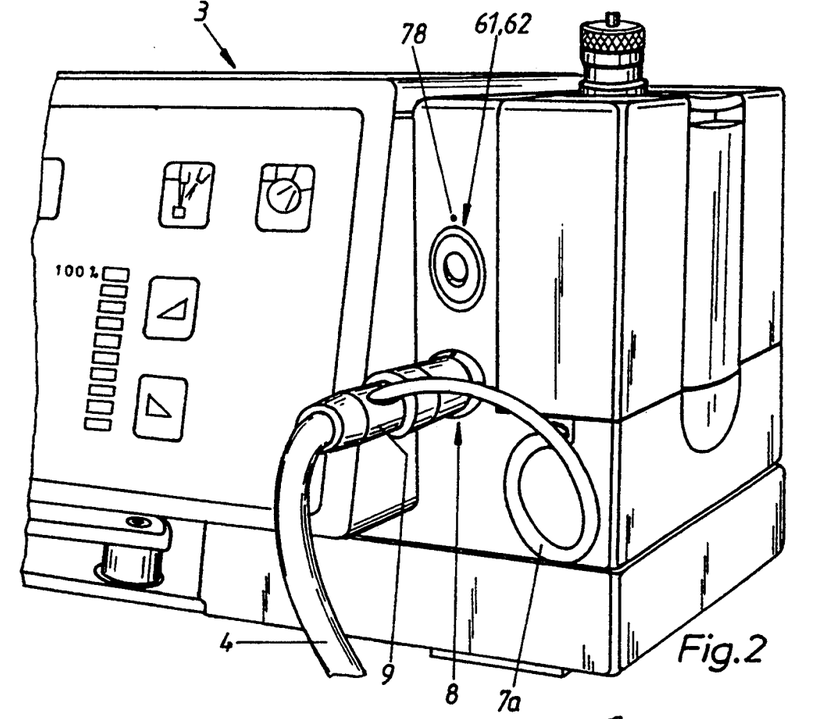
FIGS. 2 to 4 show the detail characterised in FIG. 1 by X, in enlarged perspective representations and in various functional dispositions.
Figure 3:
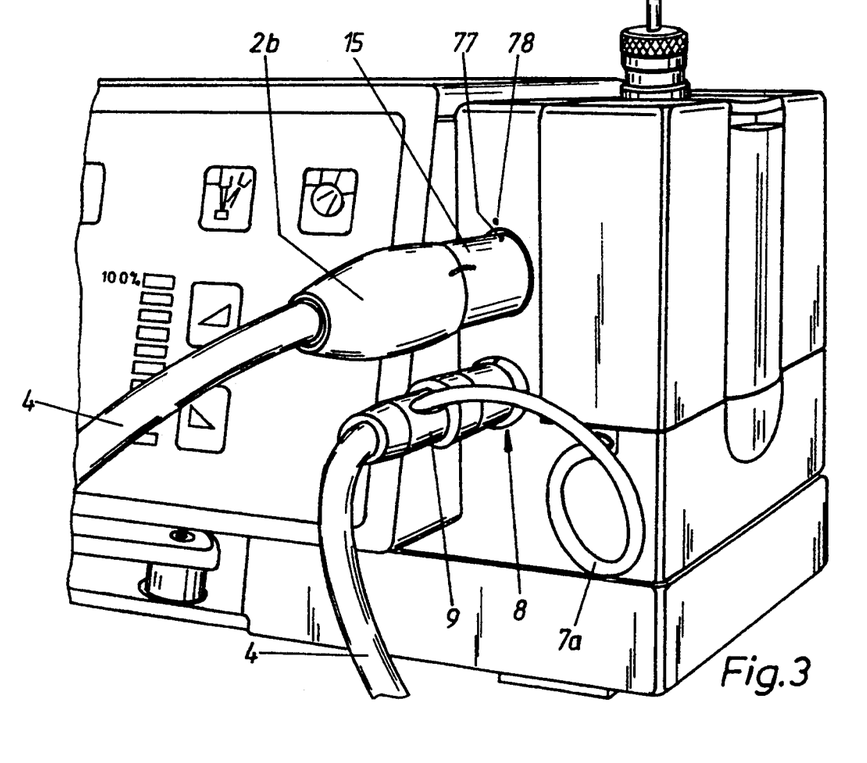
Figure 4:
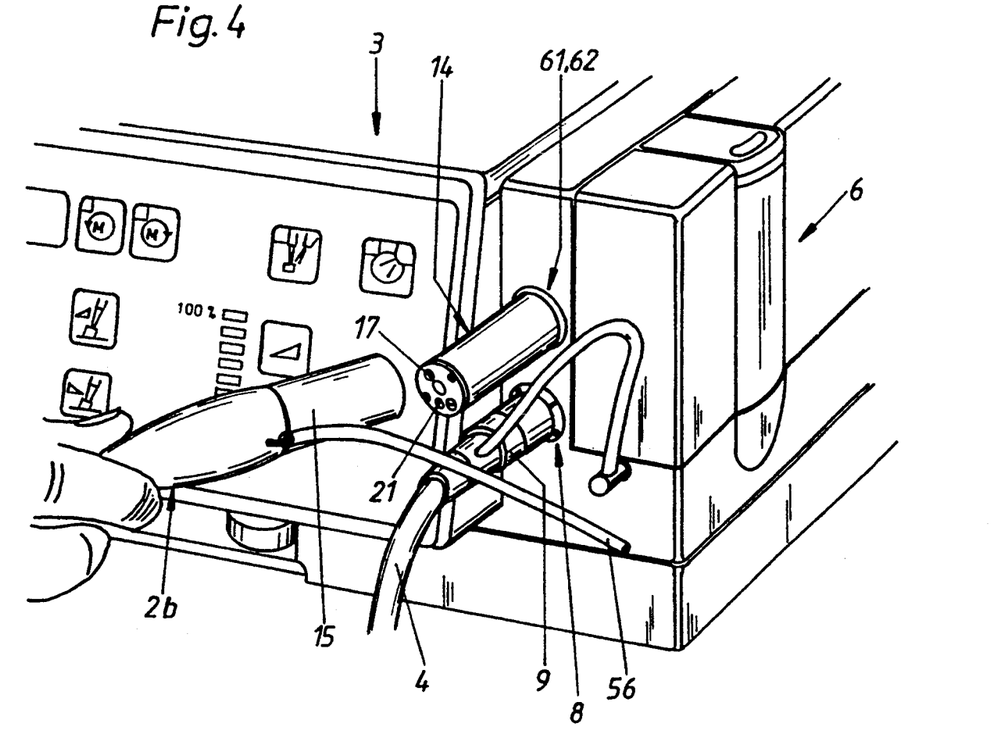

Such a delivery and return-delivery are described in the following. After the respective treatment (FIGS. 1 and 2) of the body to be treated, the tool carrier portion 2b is removed from the drive portion 2a, this occurring by release of a coupling, for example by means of the tensioning ring 51 and a corresponding coupling element associated with the tool carrier portion 2b. The tool carrier portion 2b is removed manually and directed to a sterilization process. The drive portion 2a is moved with the coupled motor cartridge 14, which is located therein, to the parking position 61 and the sleeve peg 38 is plugged into the plug-hole 65 so that the second coupling 72 closes and thus the motor cartridge 14 is secured against unintentional extraction from the receiving arrangement 62 (FIG. 2). When the pressure member 73 of the uncoupling actuating means 67 meets with the pressure piece 47, the first coupling 68 between the motor cartridge 14 and the sleeve 15 is automatically released so that the drive portion 2a can be drawn off with its sleeve 15 from the motor cartridge 14 held in the receiving arrangement 62 (FIG. 4). The motor cartridge 14 is preferably plugged into the receiving arrangement 62 in such a rotational disposition that the pressure element 73 automatically reaches the pressure piece 47. This rotational disposition can be established by means of a marking 77 on the periphery of the sleeve 15 and in the front region thereof and by a marking 78 on the receiving arrangement 62 or the connection plate 63 respectively above the plug-in bushing 64. It is, however, also possible to plug in the motor cartridge 14 in a rotationally offset position and by means of rotation bring the pressure element 73 and the pressure piece 47 into contact with each other.

Figure 7:
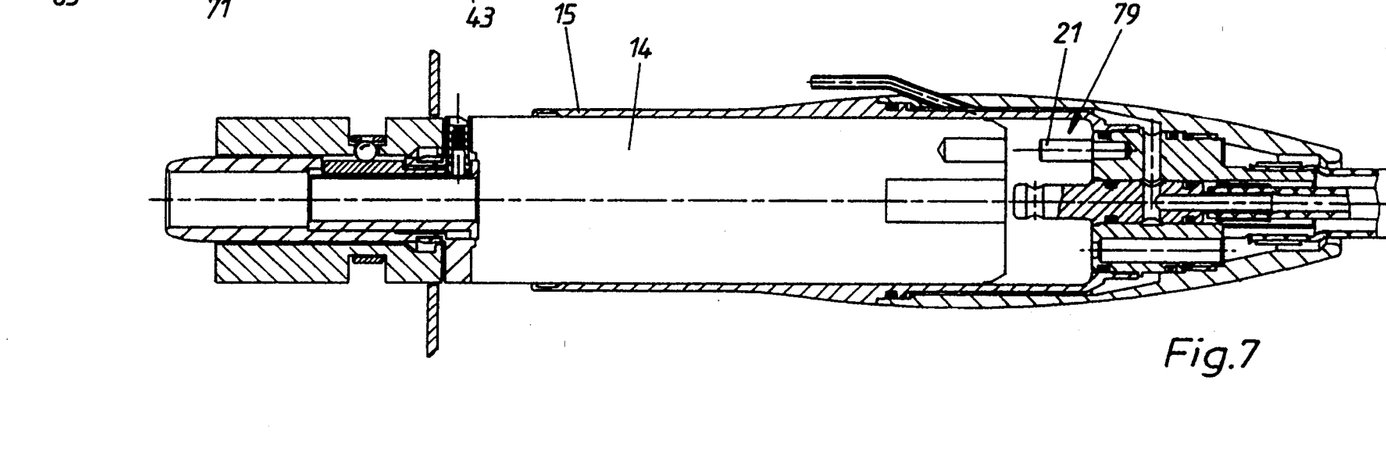

The return-delivery of the motor cartridge 14 to the drive portion 2a can be effected after the sterilization likewise with ease of handling in that the drive portion 2a is plugged with its sleeve 15 onto the motor cartridge 14 to such an extent that the rotary coupling 79, effective between the drive portion 2a and the free end face of the motor cartridge 14 and established by the pins 17, 21, is closed, FIG. 7. Subsequently, the drive portion 2a with the motor cartridge 14 is turned in one of the two directions of rotation as desired, whereby the pressure member 73 and the pressure piece 47 become disengaged and the pressure piece 47 with the locking pin 41 automatically reach their coupling position, whereby the first coupling 68 is closed. Subsequently, as a result of the tensile force when drawing the motor cartridge 14 axially out of the receiving arrangement 62 the second coupling 72 is easily undone and the drive portion 2a and the motor cartridge 14 are removed from the parking position 61 (FIG. 6). Subsequently, merely all that is further required is to attach the tool carrier portion 2b in order to carry out renewed treatment.

The protection of the motor cartridge 14 from contamination is ensured inter alia in that it is completely encapsulated in the hand piece 2 and can be deposited at the parking position 61 during the sterilization of the hand piece 2.

On account of the rapid-action coupling or plug-in coupling present between the depository portion 13 and the supporting arm 12a, the depository portion 13 can be removed and installed easily and quickly, in particular for the purposes of sterilization, if applicable with the hand piece 2 and the supply line 4.

The treatment device is suitable in particular for surgical or microsurgical treatment of human or animal bodies.

I claim:

1. Medical treatment device for a surgical treatment station, comprising a motor-operated treatment instrument having a handpiece consisting of at least two portions, one handpiece portion being connectable to a control unit by a media supply line and the other handpiece portion for receiving a treatment tool, one of the two handpiece portions containing a separable motor cartridge; a receiving arrangement in the form of a plug-in device constituting a parking place for the motor cartridge being located at the treatment station; a first coupling with coupling means for the releasable coupling of the one handpiece portion and the motor cartridge; and a second coupling with coupling means for coupling the motor cartridge and the receiving arrangement in the position in which the cartridge has been transferred to the receiving arrangement, whereby said handpiece portion supporting the motor cartridge is transferable with said cartridge from said treatment station for positioning said cartridge at said parking place and is detachable from said cartridge, and said handpiece portion is reattachable to said cartridge and returnable in conjunction therewith to said treatment station for reconnection of said cartridge with said other handpiece portion.

2. Treatment device according to claim 1, wherein the hand piece portion which has the supply line contains the motor cartridge.

3. Treatment device according to claim 2, wherein the first-mentioned handpiece portion has a sleeve which faces the front side of the other hand piece portion, and which completely covers at least a motor body of the motor cartridge.

4. Treatment device according to claim 1, wherein the receiving arrangement has an uncoupling actuating means operatively associated therewith for releasing the first coupling in the position of the motor cartridge in which the cartridge has been transferred to the receiving arrangement.

5. Treatment device according to claim 1, wherein the plug-in receiving device is in the form of a plug-in bushing.

6. Treatment device according to claim 5, wherein the motor cartridge has on a front end thereof a plug-in peg with which the cartridge is plugged into the plug-in bushing.

7. Treatment device according to claim 6, wherein the first coupling has a release-actuating member which is accessible from a front end and extends within the plug-in peg from the motor cartridge body towards the front end.

8. Treatment device according to claim 1, wherein the receiving arrangement is arranged on a front side of the control.

9. Treatment device according to claim 1, wherein said handpiece portion which is connectable to said control unit by said media supply line and the other handpiece portion which is adapted to receive a treatment tool, has said last-mentioned of the two handpiece portions containing said motor cartridge; and said coupling for releasably connecting said cartridge with the therewith associated handpiece portion.

10. Treatment instrument according to claim 9, wherein the plug-in coupling is arranged between a rear end face of the motor cartridge and the associated handpiece portion.

11. Treatment instrument according to claim 9, wherein the associated handpiece portion has a sleeve which substantially completely covers at least a cartridge body of the motor cartridge.

12. Treatment device according to claim 1, wherein the motor cartridge is insertable from the front into the first-mentioned handpiece portion and comprises on its front end a sleeve plug projecting beyond the front end of said hand-piece portion, and is pluggable into the other handpiece portion and into the plug-in receiving arrangement.

13. Treatment device according to claim 12, wherein the coupling comprising a plug-in coupling is arranged between a front end of the motor cartridge and a front end of said first-mentioned handpiece.

* * * * *